(12) United States Patent
Tamura

(10) Patent No.: US 9,918,628 B2
(45) Date of Patent: Mar. 20, 2018

(54) ACCOMMODATION FUNCTION EVALUATION APPARATUS

(71) Applicant: KABUSHIKI KAISHA TOPCON, Itabashi-ku (JP)

(72) Inventor: Takaichi Tamura, Fujimino (JP)

(73) Assignee: KABUSHIKI KAISHA TOPCON, Itabashi-ku (JP)

( * ) Notice: Subject to any disclaimer, the term of this patent is extended or adjusted under 35 U.S.C. 154(b) by 0 days.

(21) Appl. No.: 15/311,328

(22) PCT Filed: Jun. 8, 2015

(86) PCT No.: PCT/JP2015/066466
§ 371 (c)(1),
(2) Date: Nov. 15, 2016

(87) PCT Pub. No.: WO2015/198846
PCT Pub. Date: Dec. 30, 2015

(65) Prior Publication Data
US 2017/0079526 A1    Mar. 23, 2017

(30) Foreign Application Priority Data

Jun. 27, 2014  (JP) ................................. 2014-132317

(51) Int. Cl.
*A61B 3/14* (2006.01)
*A61B 3/10* (2006.01)
(Continued)

(52) U.S. Cl.
CPC ............ *A61B 3/102* (2013.01); *A61B 3/0025* (2013.01); *A61B 3/09* (2013.01); *A61B 3/10* (2013.01); *A61B 3/1005* (2013.01); *A61B 3/1173* (2013.01)

(58) Field of Classification Search
USPC .................................................. 351/200–246
See application file for complete search history.

(56) References Cited

U.S. PATENT DOCUMENTS

| 2001/0024265 A1 | 9/2001 | Fujieda |
| 2001/0035939 A1 | 11/2001 | Mihashi et al. |

(Continued)

FOREIGN PATENT DOCUMENTS

| JP | 2000-126132 A | 5/2000 |
| JP | 2001-269317 A | 10/2001 |

(Continued)

OTHER PUBLICATIONS

International Search Report dated Sep. 8, 2015 in PCT/JP2015/066466 filed Jun. 8, 2015.

*Primary Examiner* — Mohammed Hasan
(74) *Attorney, Agent, or Firm* — Oblon, McClelland, Maier & Neustadt, L.L.P.

(57) ABSTRACT

To evaluate the accommodation function of an eye in detail, an accommodation function evaluation apparatus includes an accommodative stimulus applying unit, a measurement unit, and an analyzer. The accommodative stimulus applying unit is configured to apply an accommodative stimulus to the eye. The measurement unit is configured to perform optical coherence tomography for a target site in the eye including at least part of the crystalline lens. The analyzer is configured to analyze data obtained by the optical coherence tomography of the eye, to which the accommodative stimulus is being applied, to generate evaluation information related to the accommodation function of the eye.

10 Claims, 9 Drawing Sheets

(51) Int. Cl.
*A61B 3/09* (2006.01)
*A61B 3/00* (2006.01)
*A61B 3/117* (2006.01)

(56) References Cited

U.S. PATENT DOCUMENTS

| | | |
|---|---|---|
| 2007/0052925 A1 | 3/2007 | Barth et al. |
| 2008/0252852 A1 | 10/2008 | Barth et al. |
| 2010/0118272 A1 | 5/2010 | Iwasaki et al. |
| 2012/0019780 A1* | 1/2012 | Nozato ............ A61B 3/102 351/221 |
| 2014/0168604 A1* | 6/2014 | Suzuki ............ A61B 3/14 351/208 |
| 2015/0042952 A1* | 2/2015 | Uchida ............ A61B 3/102 351/206 |
| 2015/0103316 A1* | 4/2015 | Torii ............ A61B 3/024 351/206 |

FOREIGN PATENT DOCUMENTS

| | | |
|---|---|---|
| JP | 2001-275972 A | 10/2001 |
| JP | 2007-501677 A | 2/2007 |
| WO | 2008/129991 A1 | 10/2008 |

\* cited by examiner

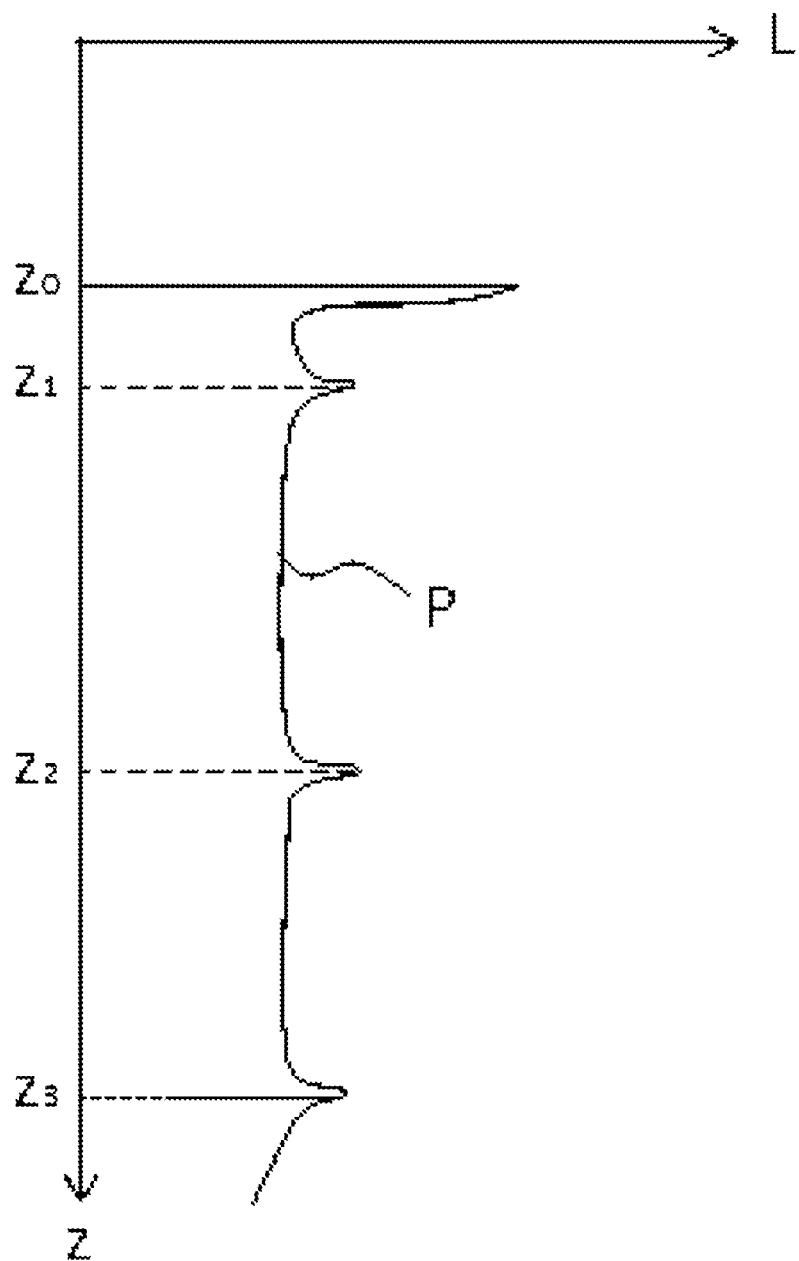

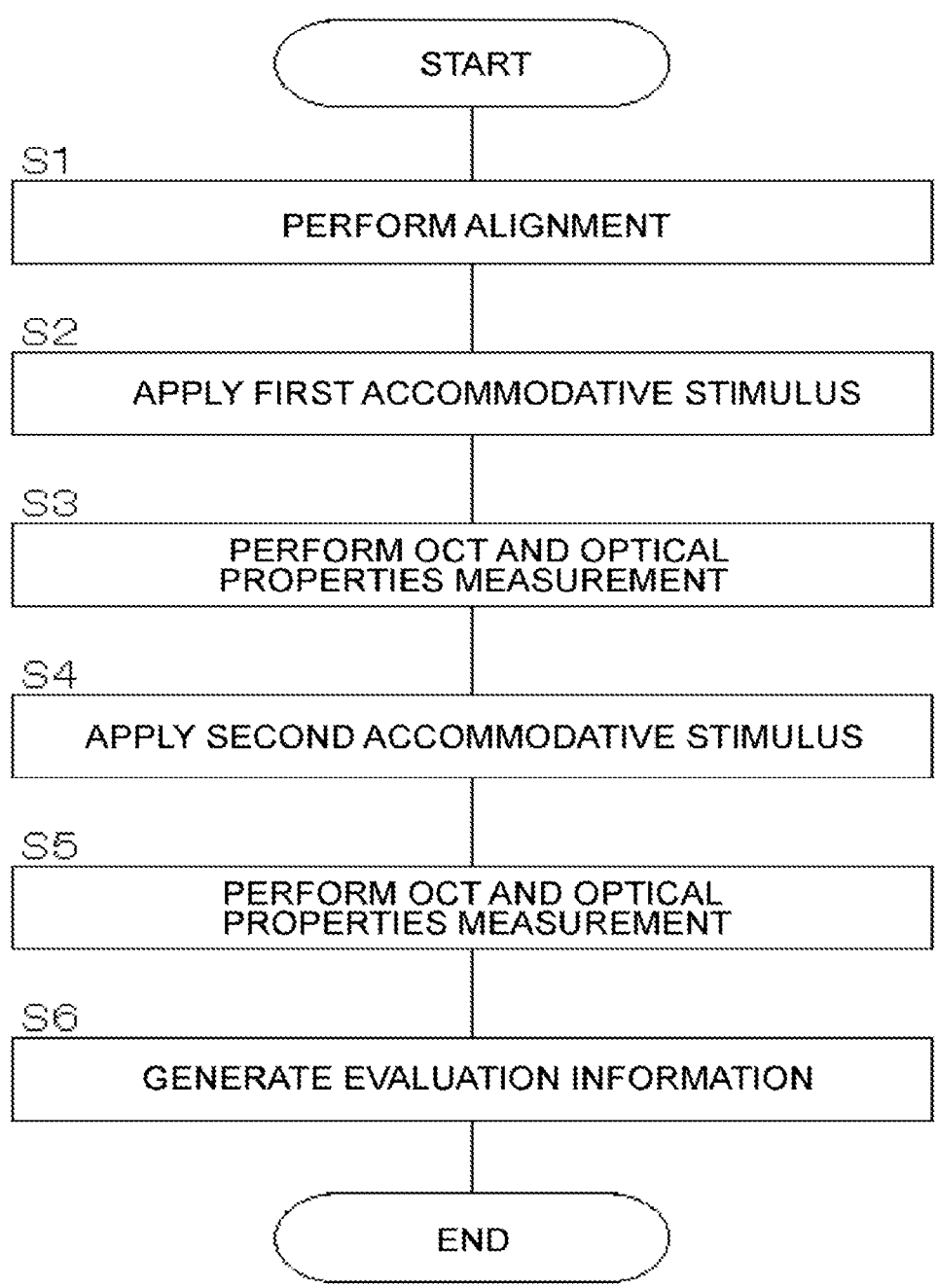

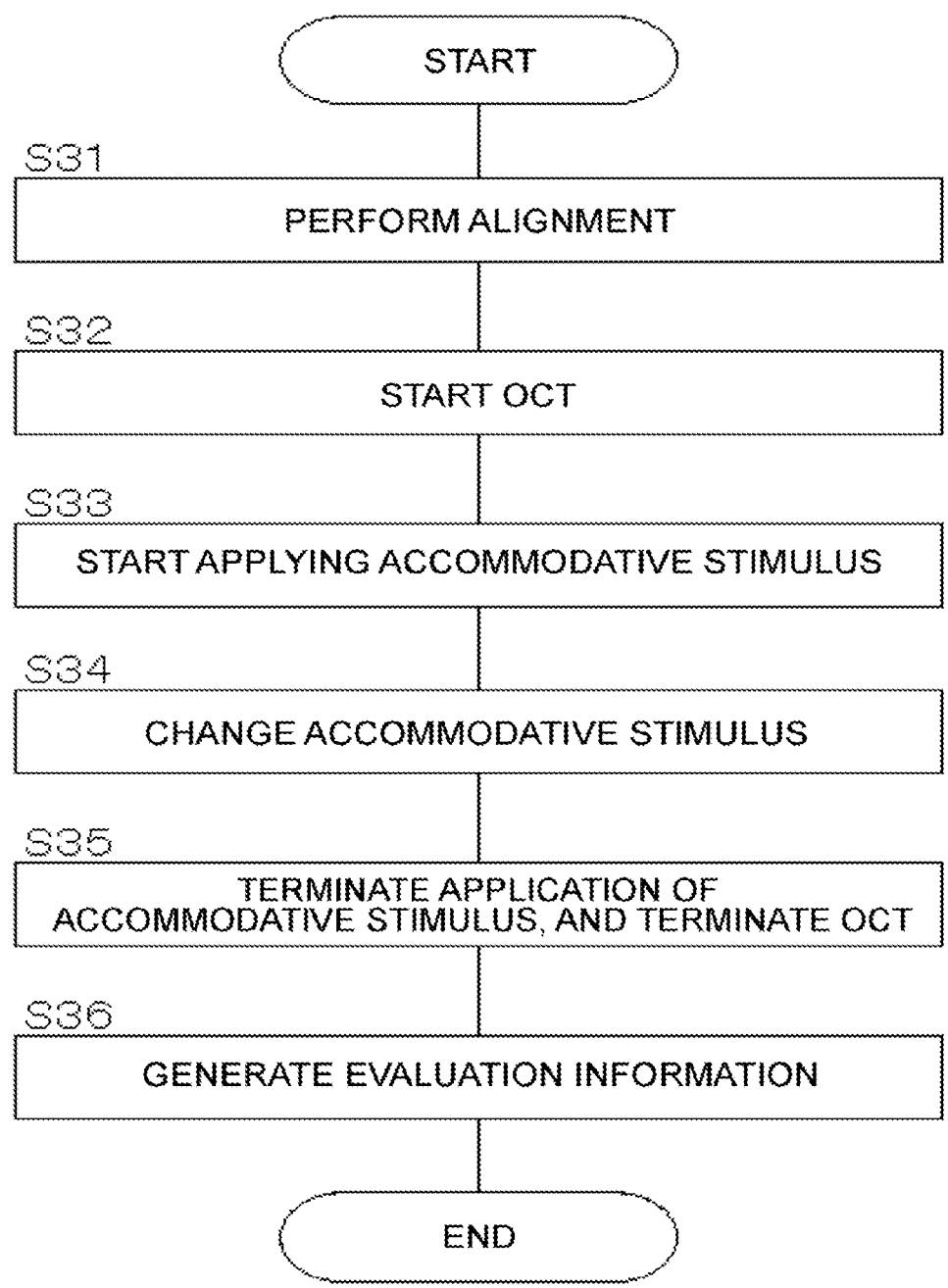

ACCOMMODATION FUNCTION EVALUATION APPARATUS

CROSS-REFERENCE TO RELATED APPLICATION

This application is based upon and claims the benefit of priority from Japanese Patent Application No. 2014-132317, filed Jun. 27, 2014; the entire contents of which are incorporated herein by reference.

FIELD

Embodiments described herein relate generally to an accommodation function evaluation apparatus for evaluating the accommodation function of a subject's eye.

BACKGROUND

Accommodation function (accommodative power) is very important in the sense of sight. The accommodation function is a function of bringing the sight into focus by changing the refractive power of the eye according to the distance to the object. The crystalline lens, Zinn's zonule, and ciliary body contribute to the change in the refractive power of the eye. The crystalline lens is a convex lens whose refractive power is variable. The Zinn's zunules are tissues that connect the crystalline lens and the ciliary body. The ciliary body is a muscle tissue. To see near objects, the ciliary muscle is contracted while the Zinn's zunules are relaxed. This results in an increase in the thickness of the crystalline lens, thereby the refractive power is increased. On the other hand, to see far objects, the ciliary muscle is relaxed while the tension in the Zinn's zunules increases. This results in reduction of the thickness of the crystalline lens, thereby the refractive power is decreased.

The accommodation function degrades due to the curing of the crystalline lens caused by aging and disease, fatigue of the ciliary muscle, and the like. As the abnormality of the accommodation function, the followings are known: accommodotonia, techno-stress eye disease (visual display terminal syndrome, video display terminal syndrome, or VDT syndrome), Barre-Lieou syndrome, paralysis of accommodation, and the like.

The accommodation function is evaluated based on the amount of aberration and the like in two states achieved by respectively inducing the subject's eye to a far point and a near point using an eye refractive power device or the like.

(Patent Document 1) Re-publication of PCT International Publication No. 2008/129991

(Patent Document 2) Japanese Unexamined Patent Application Publication No. 2000-126132

In such a conventional technology, it has been difficult to structurally evaluate whether the tissues involved in the accommodation function work in a proper way. For example, in the conventional technologies, is has not been comprehensible how the crystalline lens, which provides the accommodative power, operates in practice (i.e., how the shape of the crystalline lens changes). Accordingly, it has been difficult to evaluate the accommodation function in detail.

The object of the present invention is to provide a technology enabling the detailed evaluation of the accommodation function of the subject's eye.

According to one embodiment, an accommodation function evaluation apparatus includes: an accommodative stimulus applying unit configured to apply an accommodative stimulus to an eye; a measurement unit configured to perform optical coherence tomography for a target site in the eye including at least part of the crystalline lens; and an analyzer configured to analyze data obtained by the optical coherence tomography of the eye, to which the accommodative stimulus is being applied, to generate evaluation information related to the accommodation function of the eye.

According to one embodiment of the present invention, the accommodation function of the subject's eye can be evaluated in detail.

BRIEF DESCRIPTION OF THE DRAWINGS

FIG. 4A is a schematic diagram for explaining an example of the operation of the accommodation function evaluation apparatus of the first embodiment.

FIG. 5 is a flowchart illustrating an example of the operation of the accommodation function evaluation apparatus of the first embodiment.

FIG. 8 is a flowchart illustrating an example of the operation of the accommodation function evaluation apparatus of the second embodiment.

DESCRIPTION OF THE EMBODIMENTS

Figure 1:
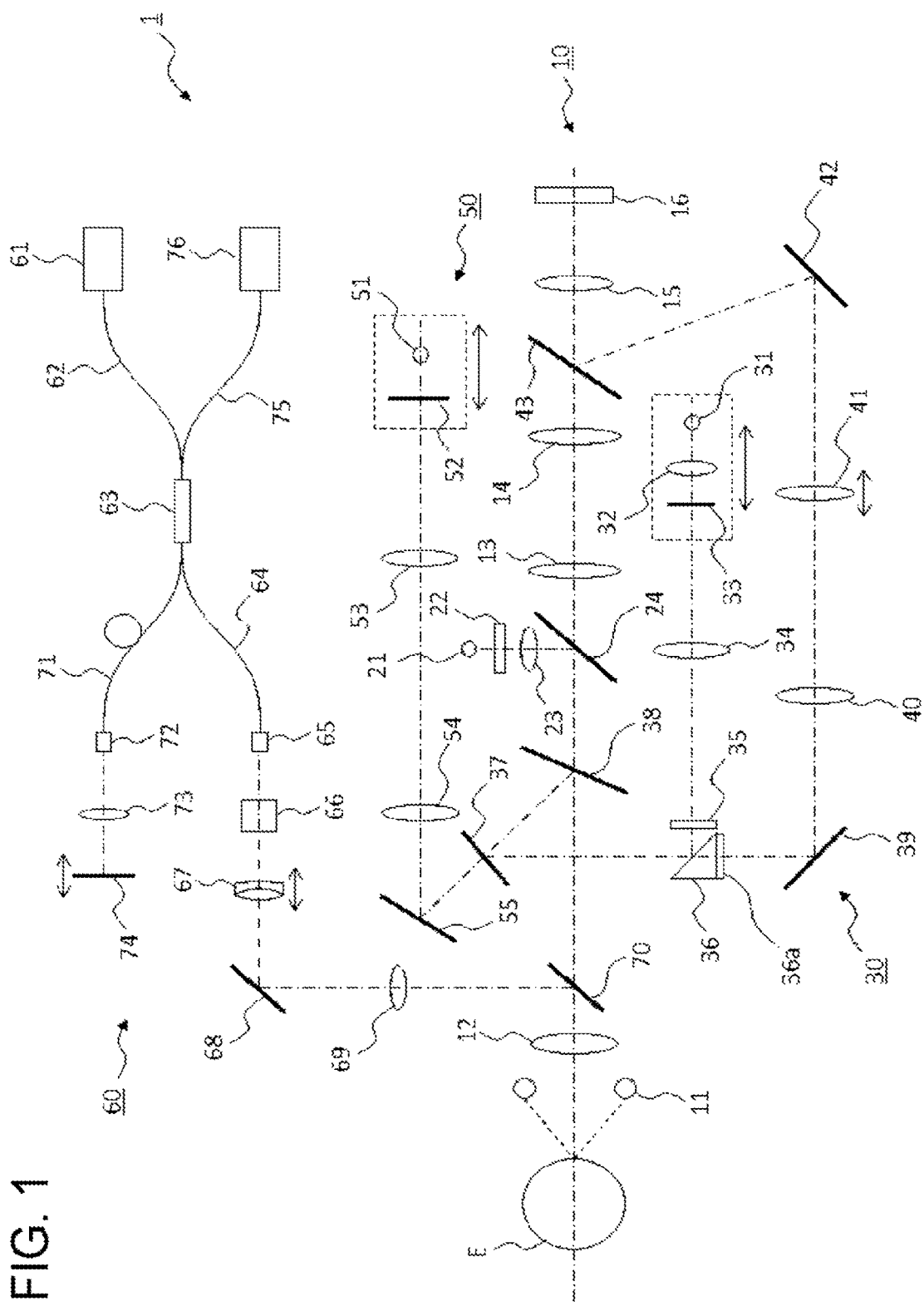
FIG. 1 is a schematic diagram illustrating an example of the configuration of an accommodation function evaluation apparatus according to the first embodiment.

Referring now to the drawings, a description is given of an accommodation function evaluation apparatus according to embodiments. An accommodation function evaluation apparatus according to one embodiment has a function of applying an accommodative stimulus to the subject's eye, a function of performing optical coherence tomography (OCT) of the subject's eye, and a function of evaluating the accommodation function of the subject's eye based on the data acquired by the use of OCT.

<First Embodiment>

[Configuration of Optical Systems]

Described below are optical systems provided in an accommodation function evaluation apparatus 1 according to an embodiment. FIG. 1 illustrates an example of the configuration of the optical systems. The accommodation function evaluation apparatus 1 includes an imaging optical system 10, a measurement optical system 30, a target projecting optical system 50, and an interference optical system 60.

(Imaging Optical System 10)

The imaging optical system 10 is used to photograph the anterior segment of the subject's eye E. The imaging optical system 10 includes an anterior eye illumination light source 11, an objective lens 12, relay lenses 13 and 14, an imaging lens 15, and an image pickup device 16.

The anterior eye illumination light source 11 includes a plurality of light sources arranged around the optical axis of the imaging optical system 10, and outputs light for illuminating the anterior eye segment. The light output from the anterior eye illumination light source 11 is irradiated to the subject's eye E, and is reflected by the anterior eye segment. The reflected light travels through the objective lens 12, the relay lenses 13 and 14, and the imaging lens 15, and detected by the image pickup device 16. At this time, the reflected light from the anterior eye segment transmits through beam splitters 70, 38, 24 and 43 (described later), and is guided to the image pickup device 16.

The beam splitter 24 is obliquely arranged between the objective lens 12 and the relay lens 13. The beam splitter 24 combines the optical path for performing anterior eye photography and an optical path for performing the alignment of the optical systems with respect to the subject's eye E. The optical path for performing alignment is provided with an alignment light source 21, an alignment target diaphragm 22, and a lens 23. The light output from the alignment light source 21 travels through the alignment target diaphragm 22 and the lens 23, is reflected by the beam splitter 24, and projected to the anterior segment of the subject's eye E through the objective lens 12. As in the conventional manner, the alignment of the imaging optical system 10 is performed with respect to the subject's eye E based on an alignment target image that appears in an image of the anterior eye segment image.

(Measurement Optical System 30)

The measurement optical system 30 optically measures an optical property of the subject's eye E. The measurement optical system 30 of this embodiment measures the refractive power of the subject's eye E. The measurement optical system 30 includes a measurement light source 31, a collimator lens 32, a ring transparent plate 33, a relay lens 34, a ring-shaped diaphragm 35, a perforated prism 36, beam splitters 37 and 38, the objective lens 12, a reflecting mirror 39, a relay lens 40, a movable lens 41, a reflecting mirror 42, the beam splitter 43, the imaging lens 15, and the image pickup device 16. The measurement optical system 30 is configured to be coaxial with the imaging optical system 10 by the beam splitters 38 and 43.

The light output from the measurement light source 31 is collimated into a parallel light beam by the collimator lens 32, and made to have a ring-shaped cross section through the ring transparent plate 33. The light then travels through the relay lens 34 and the ring-shaped diaphragm 35, is reflected by the perforated prism 36, is reflected by the beam splitter 37, and is reflected by the beam splitter 38, thereby being irradiated to the subject's eye E via the objective lens 12.

Having been irradiated to the subject's eye E, the measurement light beam having a ring-shaped cross section is reflected by the eye fundus, and is output from the subject's eye E. In this case, the cross sectional shape of the measurement light beam is deformed due to the effect of the optical system (cornea, lens, etc.) of the eyeball.

Having been output from the subject's eye E, the measurement light beam travels through the objective lens 12 and the beam splitters 38 and 37, and passes through a transparent plate 36a formed on the perforated prism 36. The measurement light beam is then reflected on the reflecting mirror 39 and travels through the relay lens 40 and the movable lens 41, and is reflected by the reflecting mirror 42 and the beam splitter 43, thereby being detected by the image pickup device 16 through the imaging lens 15. By analyzing the size, shape, and the like of the cross section of the detected measurement light beam, the aberration of the subject's eye E (the spherical degree, the degree of astigmatism, the astigmatic axis, etc.) is obtained. Such a process is performed similarly to the conventional manner. In other words, the accommodation function evaluation apparatus 1 functions as a refractometer.

(Target Projecting Optical System 50)

The target projecting optical system 50 presents a variety of visual targets to the subject's eye E. The target projecting optical system 50 includes a target light source 51, a target plate 52, relay lenses 53 and 54, a reflecting mirror 55, the beam splitter 38, and the objective lens 12. The target projecting optical system 50 is configured to be coaxial with the imaging optical system 10 and the measurement optical system 30 by the beam splitter 38.

The target plate 52 includes, for example, a turret plate, a liquid crystal display of transmissive type, or the like, and is configured such that various visual targets such as a fixation target and optotypes for eye test can be selectively arranged in the optical path. The light output from the target light source 51 travels through the above components of the target projecting optical system 50, and is projected to the fundus of the subject's eye E.

The target light source 51 and the target plate 52 are movable in the direction along the optical axis of the target projecting optical system 50. Thereby, the distance at which the subject can visually recognize a visual target with the eye E is changed. In this way, the target projecting optical system 50 can be used to apply an accommodative stimulus to the subject's eye E.

(Interference Optical System 60)

The interference optical system 60 is used for OCT of the subject's eye E. The interference optical system 60 includes a light source unit 61, an optical fiber 62, a fiber coupler 63, an optical fiber 64, a collimator 65, an optical scanner 66, a focusing lens 67, a reflecting mirror 68, a relay lens 69, the beam splitter 70, the objective lens 12, an optical fiber 71, a collimator 72, a condensing lens 73, a reference mirror 74, an optical fiber 75, and a detector 76.

Any system of OCT is applicable in this embodiment. If swept source OCT system is applied, a wavelength-swept light source, which can modulate the output wavelength at a high speed, is used as the light source unit 61, and an optical detector such as a balanced photo detector is used as the detector 76. If spectral domain OCT system is applied, a broadband light source (low-coherence light source) is used as the light source unit 61, and a spectroscope for detecting the spectra is used as the detector 76. Incidentally, other types of OCT system such as time domain OCT vsystem or full-field OCT system (en-face OCT system) can also be utilized.

The fiber coupler 63 connects the optical fiber 62 that forms an optical path extending from the light source unit 61, the optical fiber 64 that forms part of an optical path extending toward the subject's eye E, the optical fiber 71 that forms part of an optical path extending toward the reference mirror 74, and the optical fiber 75 that forms an optical path extending toward the detector 76. The fiber coupler 63 has at least two functions. The first function is a function of splitting the light output from the light source unit 61 into light toward the subject's eye E (measurement light) and light toward the reference mirror 74 (reference light). The second function is a function of combining the measurement light returning from the subject's eye E and the returning light from the reference mirror 74 (that is, a function of causing the measurement light returning from the subject's eye E and the returning light from the reference mirror 74 to interfere with each other). The optical path of the measurement light is referred to as a measurement optical path or a measurement arm, while the optical path of the reference light is referred to as a reference optical path or a reference arm.

The measurement arm includes the optical fiber 64, the collimator 65, the optical scanner 66, the focusing lens 67, the reflecting mirror 68, the relay lens 69, the beam splitter 70, and the objective lens 12.

The collimator 65 is located at an end of the optical fiber 64. The collimator 65 collimates the measurement light output from the optical fiber 64 into a parallel light beam, and converts the measurement light returning from the subject's eye E into convergent light. Thus, the convergent measurement light enters the optical fiber 64.

The optical scanner 66 changes the traveling direction of the measurement light to scan the subject's eye E with the measurement light. The optical scanner 66 includes, for example, a pair of single-axis deflectors or a two-axis deflector. Examples of such an optical deflector include a galvanometer scanner, a resonant mirror, an MEMS mirror, a polygon mirror, and the like.

The focusing lens 67 includes one or more lenses configured to be movable along the direction of the optical axis of the measurement light. With the movement of the focusing lens 67, the focusing position of the measurement light (beam waist position) changes.

The beam splitter 70 combines the measurement arm and the optical path of the imaging optical system 10. Thereby, the imaging optical system 10, the measurement optical system 30, the target projecting optical system 50, and the interference optical system 60 are arranged coaxially.

The reference arm is provided with the optical fiber 71, the collimator 72, the condensing lens 73, and the reference mirror 74.

The collimator 72 is located at an end of the optical fiber 71. The collimator 72 collimates the reference light output from the optical fiber 71 into a parallel light beam, and converts the reference light returning from the reference mirror 74 into convergent light. Thus, the convergent reference light enters the optical fiber 71.

The condensing lens 73 forms an image of the reference light, which has been collimated into a parallel light beam by the collimator 72, on the reflection surface of the reference mirror 74. The condensing lens 73 also converts the reference light returning from the reference mirror 74 into a parallel light beam.

The reference mirror 74 is located in a position optically conjugate to the site of the subject's eye E to be subjected to OCT (sometimes referred to as a "target site"). The reference mirror 74 and the condensing lens 73 are configured to be integrally movable along the direction of the optical axis of the reference light. It is assumed in this embodiment that the subject site includes at least part of the crystalline lens. That is, the target site includes at least part of the crystalline lens, and may further include at least part of another site (e.g. the cornea, the iris, the vitreous body, etc.). Further, the target site may include the ciliary body or the Zinn's zonule.

Although FIG. 1 illustrates one reference mirror (the reference mirror 74, first reference mirror), there may be two or more reference mirrors. For example, a configuration may be introduced in which a beam splitter (e.g. a half mirror) is arranged between the collimator 72 and the reference mirror 74, and a condensing lens and a second reference mirror are arranged on the optical path branched by the beam splitter. The second reference mirror may be arranged in a position conjugate to a second target site of the subject's eye E. As well as the target site (the first target site) related to the first reference mirror 74, the second target site is to be subjected to OCT, and may be, for example, the vitreous body, the retina, the choroid, or the like. The second reference mirror and the condensing lens are configured to be movable along the direction of the optical axis of the branched optical path. Similarly, there may be provided three or more reference mirrors.

The light output from the light source unit 61 is guided through the optical fiber 62 to the fiber coupler 63. The fiber coupler 63 splits the light into two portions.

The light (measurement light) guided to the optical fiber 64 by the fiber coupler 63 is collimated into a parallel light beam by the collimator 65. Having been deflected by the optical scanner 66, the light then travels through the focusing lens 67, and is reflected by the reflecting mirror 68. Thereafter, the light is relayed by the relay lens 69, reflected by the beam splitter 70, and thereby irradiated to the subject's eye E via the objective lens 12. The measurement light irradiated to the subject's eye E is reflected and scattered in various tissues and tissue boundaries of the subject's eye E. The measurement light returning from the subject's eye E is guided through the measurement arm in the opposite direction and returns to the fiber coupler 63. Incidentally, the measurement light returning from the subject's eye E includes reflected light and backscattering light from the subject's eye E. In fluorescence imaging performed by using a fluorescent agent, the return light includes fluorescence excited by the measurement light.

On the other hand, the light (reference light) guided to the optical fiber 71 by the fiber coupler 63 is collimated into a parallel light beam by the collimator 72, and is focused on the reflecting surface of the reference mirror 74 by the condensing lens 73. The reference light reflected by the reference mirror 74 is converted into a parallel light beam by the condensing lens 73. The reference light is then converted into convergent light by the collimator 72 and enters the optical fiber 71. Thus, the reference light returns to the fiber coupler 63 through the optical fiber 71.

When there are provided two or more reference mirrors, a configuration may be introduced in which: the reference light, which has been collimated into a parallel light beam by the collimator 72, is split into two or more reference light beams by one or more beam splitters; the reference light beams each reflected by corresponding one of the reference mirrors are combined by the one or more beam splitters; and the combined reference light enters the optical fiber 71 through the collimator 72.

The fiber coupler 63 causes the measurement light returning from the subject's eye E and the reference light returning from the reference mirror 74 to interfere with each other. Interference light thus generated includes information on the target site (the crystalline lens, etc.) of the subject's eye E conjugate to the reference mirror 74. If two or more reference mirrors are provided, the interference light includes information on two or more target sites conjugate to the respective reference mirrors. The interference light is guided to the detector 76 through the optical fiber 75. In the case of swept source OCT system, the detector 76 detects the intensity of the interference light. In the case of spectral domain OCT system, the detector 76 detects the spectral distribution of the interference light.

Although not illustrated, the interference optical system 60 is provided with an attenuator and a polarization controller. The attenuator is provided, for example, on the optical fiber 71 to adjust the light amount of the reference light guided to the optical fiber 71. For example, the polarization controller applies stress to the optical fiber 71 in a loop form from the outside to adjust the polarization state of the reference light guided to the optical fiber 71. In addition, the interference optical system 60 may further be provided with a variety of known devices applicable to OCT.

[Configuration of Control System]

Figure 2:
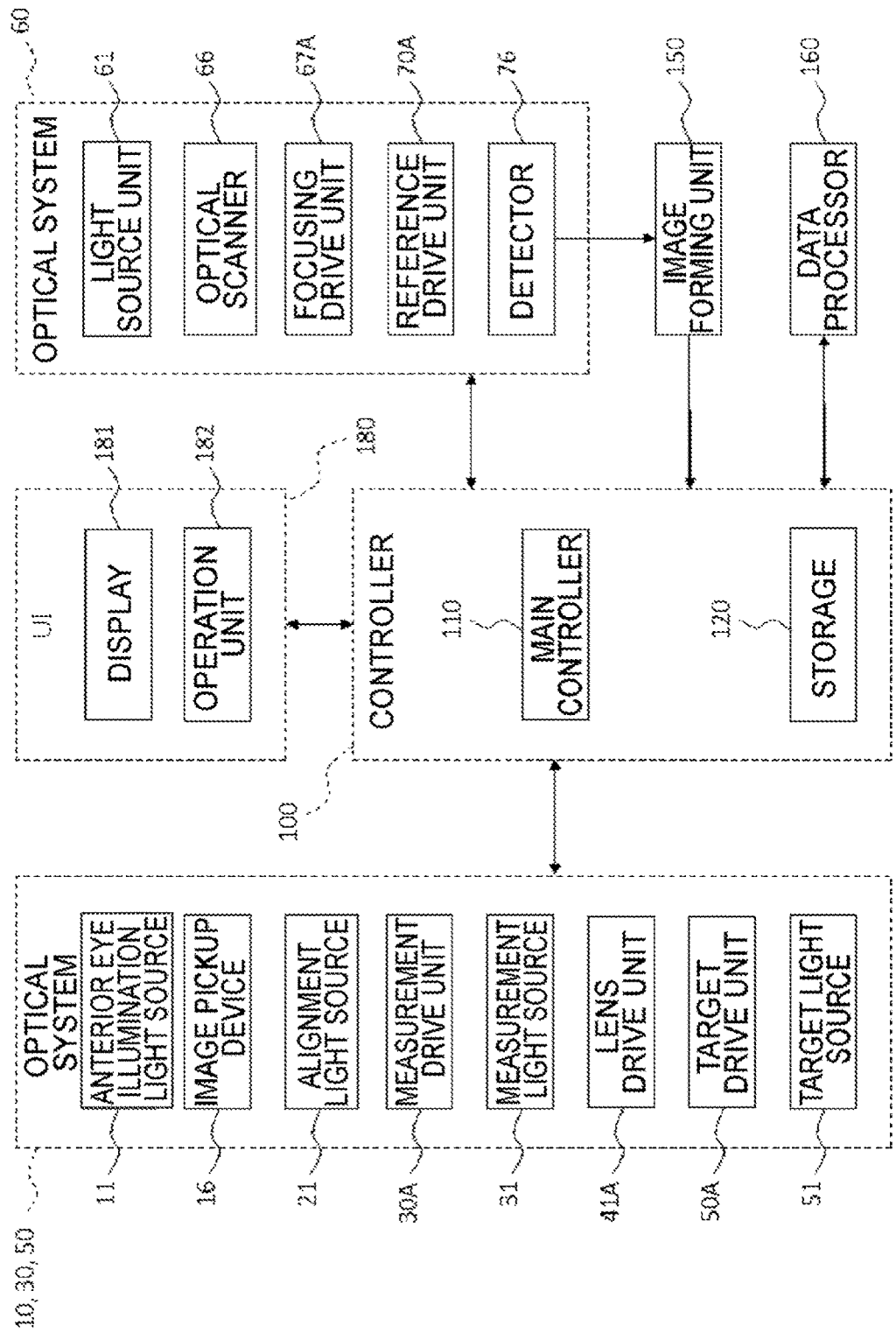
FIG. 2 is a schematic diagram illustrating an example of the configuration of the accommodation function evaluation apparatus of the first embodiment.
Figure 3:
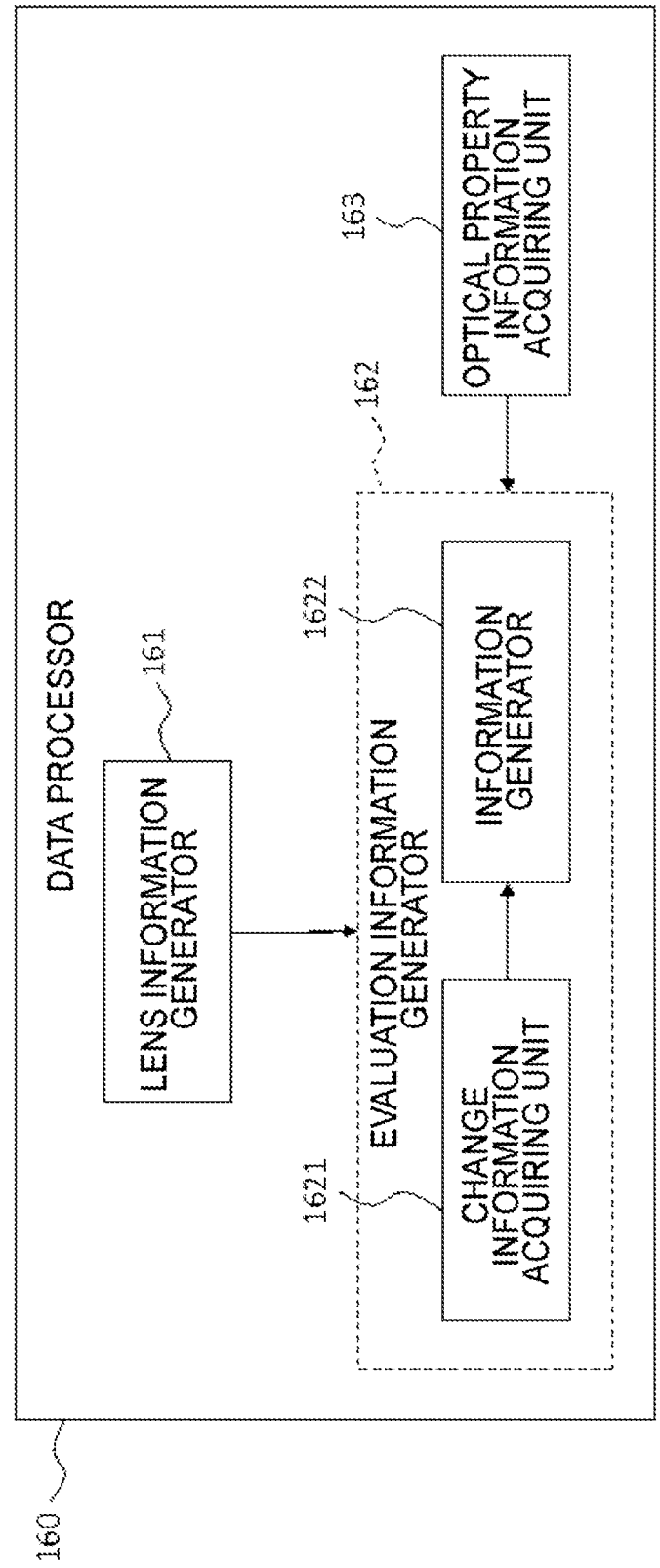
FIG. 3 is a schematic diagram illustrating an example of the configuration of the accommodation function evaluation apparatus of the first embodiment.

FIGS. 2 and 3 illustrate an example of the configuration of the control system of the accommodation function evaluation apparatus 1.

(Controller 100)

A controller 100 is center of the control system of the accommodation function evaluation apparatus 1. The controller 100 includes, for example, a processor, a storage device, a communication interface, and the like. The storage device stores computer programs and data for control and operation. The controller 100 is provided with a main controller 110 and a storage 120.

(Main Controller 110)

The main controller 110 controls each unit of the accommodation function evaluation apparatus 1. For example, the main controller 110 controls the operation of components illustrated in FIG. 1, such as the anterior eye illumination light source 11, the image pickup device 16, the alignment light source 21, the measurement light source 31, the target light source 51, the light source unit 61, the optical scanner 66, the detector 76, and the like. Although not illustrated, the main controller 110 controls the attenuator and the polarization controller mentioned above.

The main controller 110 controls the movement of the optical elements. For example, the main controller 110 controls a measurement drive unit 30A to move the measurement light source 31, the collimator lens 32, and the ring transparent plate 33 in the optical axis direction. The main controller 110 also controls a lens drive unit 41A to move the movable lens 41 in the optical axis direction. Besides, the main controller 110 controls a target drive unit 50A to move the target light source 51 and the target plate 52 in the optical axis direction. Further, the main controller 110 controls a focusing drive unit 67A to move the focusing lens 67 in the optical axis direction. In addition, the main controller 110 controls a reference drive unit 70A to move the lens 73 and the reference mirror 74 in the optical axis direction. Each of these drive units includes, for example, an actuator such as a pulse motor, and a transmission mechanism for transmitting a driving force generated by the actuator to the corresponding optical element.

Although not illustrated, the accommodation function evaluation apparatus 1 may include a mechanism for moving the optical system (optical system drive unit). The optical system drive unit includes, for example, a mechanism for moving the optical system three-dimensionally (i.e., in the vertical direction, the lateral direction, and the front-back direction), a mechanism for rotating the optical system, or the like. The main controller 110 controls the optical system drive unit to control the movement of the optical system.

The main controller 110 performs a process of writing data to the storage 120, and a process of retrieving data from the storage 120.

(Storage 120)

The storage 120 stores various data. Examples of such data stored in the storage 120 include, for example, image data of the anterior eye segment image, data acquired by OCT (reflection intensity profile, image data, etc.), measurement data of the subject's eye, subject's eye information, and the like. The subject's eye information includes information related to the subject, such as patient ID and name, and information related to the subject's eye, such as identification information of the left eye/right eye.

In one embodiment, the storage 120 stores reference data related to the crystalline lens. The reference data may include information indicating a reference position of a portion of the crystalline lens. Also, the reference data may include information indicating a reference shape of a portion of the crystalline lens. The portion of the crystalline lens may include, for example, at least part of the front surface and/or at least part of the rear surface of the crystalline lens.

The reference position indicates, for example, the position of the crystalline lens when a predetermined accommodative stimulus (reference accommodative stimulus) is being applied to the eye. The reference accommodative stimulus can be set in an arbitrary way. For example, an accommodative stimulus corresponding to a far point may be used as the reference accommodative stimulus. The reference position may be information in any form. In one example, the reference position is the position of a target site of the crystalline lens (site corresponding to the part mentioned above such as the front surface, the rear surface) relative to a predetermined position in a frame of an OCT image (e.g., the upper end position, the lower end position, or the center position in the z direction). In another example, the reference position is the position of a target site of the crystalline lens relative to a predetermined image position in an OCT image (e.g., the corneal vertex position, the pupil center position, or the lens center position). Alternatively, the reference position can also be obtained as data position in the reflection intensity profile (e.g., a coordinate value in the depth direction and/or a coordinate value in the scanning direction).

The reference shape indicates, for example, the shape of the crystalline lens when the reference accommodative stimulus is being applied to the eye. The reference shape may be information in any form. In one example, the reference shape is information indicating the shape of a target site of the crystalline lens in an OCT image. The shape information may be information representing the shape of the target site as is, or may be information representing the approximate shape thereof. The shape information may be represented by an image or an arrangement of pixels, or it may be expressed mathematically using a graph or a mathematical formula. Examples of such a mathematical expression include the curvature, the radius of curvature, the tangential direction (differential value or slope), the normal direction, and the like.

The reference data may be provided for each subject, or may be provided as standard data (general data or statistical data). When the reference data is provided for each subject, the subject (e.g., left and right eyes of the subject) is examined in advance. In this preliminary examination, for example, OCT is performed with respect to the eye to which the reference accommodative stimulus is being applied. Alternatively, if an examination performed in the past is applicable to the reference data, the result of the examination can be used as the reference data.

On the other hand, if the standard data is provided as the reference data, the standard data may be generated by statistically processing a plurality of data sets obtained by examining a plurality of eyes. This statistical processing includes, for example, averaging calculation. There may be provided a plurality of pieces of standard data. For example, it is possible to produce a plurality of pieces of standard data according to a predetermined attribute such as sex, age, disease name, characteristic values of an eyeball, and the like. Having received input of the attribute of the subject's eye, the main controller 110 selects standard data that corresponds to this attribute. At this time, the main controller 110 can select a single piece of standard data or two or more pieces of standard data. In the latter case, the two or more pieces of standard data can be combined to create new standard data. Alternatively, standard data may be prepared in advance with respect to each combination of a plurality of attributes.

(Image Forming Unit 150)

The detector 76 detects the interference light obtained by superposing the return light of the measurement light and the reference light, and outputs a signal. This signal is input to an image forming unit 150. The image forming unit 150 obtains the reflection intensity profiles of the A-lines at the irradiation positions (scanning points) of the measurement light based on the signals from the detector 76. Besides, the image forming unit 150 processes the reflection intensity profile of each of the A-lines to form image data of the A-line image (A-scan image). The image forming unit 150 arranges a plurality of A-scan images according to the scan pattern of the measurement light (arrangement of scanning points). Thereby, the image forming unit 150 forms image data of a two-dimensional cross sectional image (B-scan image) in which the A-scan images are arranged one-dimensionally (arranged in a linear fashion or in a curved fashion), image data (stack data) of a three-dimensional cross sectional image in which the A-scan images are arranged two-dimensionally.

As in the conventional technology, the image forming process includes noise removal (noise reduction), filtering, fast Fourier transform (FFT), and the like. The image forming unit 150 includes, for example, a hardware circuit, a processor to run software for image formation, or the like. Incidentally, sometimes "image data" is regarded in the same light as "image" in this specification.

(Data Processor 160)

A data processor 160 performs various types of data processing. For example, the data processor 160 applies various types of image processing and/or analysis processing to an OCT image, an anterior eye segment image, or the like. Examples of such processing include brightness correction, dispersion correction, and the like. The data processor 160 performs interpolation processing or the like on the stack data formed by the image forming unit 150 to form volume data (voxel data). The data processor 160 generates display data by performing rendering on the stack data or the volume data. The data processor 160 includes a hardware circuit, a processor to run software for data processing, or the like.

The data processor 160 is an example of an "analyzer". More specifically, the data processor 160 analyzes data obtained by performing OCT on the subject's eye E to which an accommodative stimulus is being applied, thereby generating evaluation information regarding the accommodation function of the subject's eye E. For this purpose, the data processor 160 includes a (crystalline) lens information generator 161, an evaluation information generator 162, and an optical property information acquiring unit 163.

Now, a description is given of examination performed in this embodiment. First, an accommodative stimulus is applied to the subject's eye E. In this embodiment, the accommodative stimulus is applied by the use of the target projecting optical system 50. More specifically, the accommodation function evaluation apparatus 1 moves the target light source 51 and the target plate 52 by the target drive unit 50A to guide the focal point of the subject's eye E to a desired position. With this, a desired accommodative force is induced.

Then, the accommodation function evaluation apparatus 1 performs OCT of the subject's eye E to which the accommodative stimulus is being applied. In this process, one or more accommodative stimuli are applied to the subject's eye E. If a single accommodative stimulus is applied, OCT is performed while the accommodative stimulus is being applied. Then, the evaluation of the accommodation function is carried out based on the data obtained by OCT and the reference data stored in the storage 120. On the other hand, when two or more accommodative stimuli corresponding to different focus positions are applied, OCT is performed while each of the accommodative stimuli is being applied by sequentially switching the accommodative stimuli. Thereby, two or more pieces of data corresponding to the respective accommodative stimuli are acquired. Then, the evaluation of the accommodation function is performed based on the two or more pieces of data acquired. At this time, the evaluation may be performed in consideration of the reference data.

The data processor 160 performs the following processing to acquire information (change information) indicating a change in the crystalline lens due to changes in the accommodative stimuli, and generates the evaluation information based on the change information.

(Lens Information Generator 161)

Based on data acquired by OCT of the subject's eye E to which the accommodative stimulus is being applied, the lens information generator 161 generates (crystalline) lens information indicating the position and/or shape of an area corresponding to a portion of the crystalline lens.

The OCT data to be analyzed may be a signal output from the detector 76 or any data obtained by processing the signal. For example, the OCT data is the reflection intensity profile or image data. Besides, the portion of the crystalline lens may include at least a portion of the front surface and/or at least a portion of the rear surface of the crystalline lens.

The position of the region corresponding to a portion of the crystalline lens may be set in a way similar to that in the case of the reference data. For example, the position of the region corresponding to a portion of the crystalline lens may be the position of the target site of the crystalline lens relative to a predetermined position in a frame of an OCT image, the position of the target site of the crystalline lens relative to a predetermined image position in an OCT image, a data position in the reflection intensity profile, or the like.

The shape of the region corresponding to a portion of the crystalline lens may be set in a way similar to that in the case of the reference data. For example, the shape of the region corresponding to a portion of the crystalline lens may be information representing the shape of the target site as is, information representing the approximate shape thereof. Also, the shape may be represented by an image or an arrangement of pixels, or it may be expressed mathematically using a graph and a mathematical formula.

Described below is an example of processing performed when OCT data is a reflection intensity profile. It is assumed as an example that OCT data is a reflection profile P illustrated in FIG. 4A. The lens information generator 161 specifies the depth position of a predetermined site of the subject's eye E based on the feature values of the reflection profile P (greatest value, least value, maximum value, minimum value, etc.), the shape of the reflection profile P, anatomical data, clinical data, or the like of an eye (e.g., common or individual association between a tissue and a depth position (z-coordinate values)), or the like.

For example, the lens information generator 161 specifies the minimum z-coordinate value $z_0$ in which the reflected light amount L is nonzero, and determines it as the position of the corneal surface (corneal front surface) in the corresponding measurement position (A-line). Alternatively, the lens information generator 161 specifies the z-coordinate value $z_0$ in which the reflected light amount L takes the maximum value, and determines it as the position of the corneal surface in the corresponding A-line. Alternatively, the lens information generator 161 specifies the z-coordinate value $z_0$ of the first peak from the shallow side (−z side) toward the deep side (+z side), and determines it as the position of the corneal surface in the corresponding A-line. Similarly, the lens information generator 161 specifies the z-coordinate values $z_1$, $z_2$, and $z_3$ of the second, third and fourth peaks, respectively. Further, the lens information generator 161 determines the z-coordinate values $z_1$, $z_2$, and $z_3$ as the position of the corneal rear surface, the position of the lens front surface, and the position of the lens rear surface, respectively, in the corresponding A-line.

Incidentally, it is possible to discriminate the case in which the measurement light passes through the pupil and the case in which the measurement light is incident on the iris, and to switch the types of processing according to the result of the discrimination. Such a discrimination process is performed based on, for example, the positions of the scanning points (A-lines) in the scan pattern, and the position of the pupil (or the iris) specified by analyzing the anterior eye segment image captured by the imaging optical system 10. FIG. 4A illustrates an example in which the measurement light passes through the pupil. In this case, a peak corresponding to the iris is not detected. Meanwhile, although not illustrated, when the measurement light is incident on the iris, the first and second peaks similarly correspond to the front and rear surfaces of the cornea, respectively, and the third peak corresponds to the iris front surface. If a light source with relatively high penetration depth is used, for example, the iris rear surface is detected as the fourth peak, the lens front surface is detected as the fifth peak, and the lens rear surface is detected as the sixth peak.

Described below is an example of processing performed when OCT data is image data. It is assumed as an example that OCT data is an image G illustrated in FIG. 4B. The image G is formed by a plurality of pieces of A-scan data (A-scan images) arranged in the x direction. Each piece of the A-scan data is image data obtained by assigning brightness values to the values of the light amount in the reflection profile. A-scan data $A_k$ arranged in the x-coordinate value $x_k$ in the image G corresponds to the reflection profile P in FIG. 4A. A reference code $H_0$ indicates an image area corresponding to the cornea front surface. A reference code $H_1$ indicates an image area corresponding to the cornea rear surface. A reference code $H_2$ indicates an image area corresponding to the lens front surface. A reference code $H_3$ indicates an image area corresponding to the lens rear surface.

The lens information generator 161 specifies the depth position of a predetermined site of the subject's eye E based on the pixel values (brightness values) of the image G, the form (size, shape, position of tissue, etc.) of the object rendered in the image G, or the like. For example, the lens information generator 161 performs a segmentation process known in the OCT field to specify the image area $H_0$ corresponding to the corneal front surface, and thereby specifies the depth position of the image area $H_0$. The depth position of the image area $H_0$ may be represented by one or more values of a plurality of positions corresponding to a plurality of pixels that constitute the image area $H_0$ (e.g. greatest value, least value, maximum value, minimum value, etc.), or one or more values obtained by performing operation process on the plurality of positions (e.g., statistics such as mean, median, and mode, etc.).

Note that an image area corresponding to a predetermined site (the cornea, crystalline lens, or their boundaries, etc.) is specified. When this specification process is performed automatically, the lens information generator 161 determines the image area of a predetermined site and other image areas based on the pixel values (brightness values), the characteristics, or the like of the OCT data. The process includes, for example, threshold processing, pattern matching, or the like.

Part of the specification process can be performed manually. In that case, the main controller 110 displays a cross sectional image on a display 181. The user recognizes an image area corresponding to a predetermined tissue through the observation of the cross sectional image displayed, and designates it by using an operation unit 182. The image area can be specified by, for example, inputting a plurality of points on the contour of the image area corresponding to the predetermined tissue with a pointing device such as a mouse. The lens information generator 161 obtains a curve that connects the input points. This curve is, for example, an approximate curve such as the spline curve or Bezier curve. An area defined by these curves is set to be the image area corresponding to the predetermined tissue. As another example, the contour may be input by using a pointing device.

The lens information generator 161 can generate lens information from the information acquired by the above process. For example, the lens information generator 161 performs the process illustrated in FIG. 4A for each A-line data, and acquires the front surface position ($z_2$) and the rear surface position ($z_3$) of the crystalline lens with respect to each A-line position (the position of the scanning point). Thus, the lens information generator 161 can generate the lens information including them. In addition, based on a plurality of front surface positions and a plurality of rear surface positions of the crystalline lens with respect to a plurality of A-lines, the lens information generator 161 obtains information indicating the shape of the front surface and the shape of the rear surface of the crystalline lens. Thereby, the lens information generator 161 can generate the lens information including the information obtained.

Figure 4B:
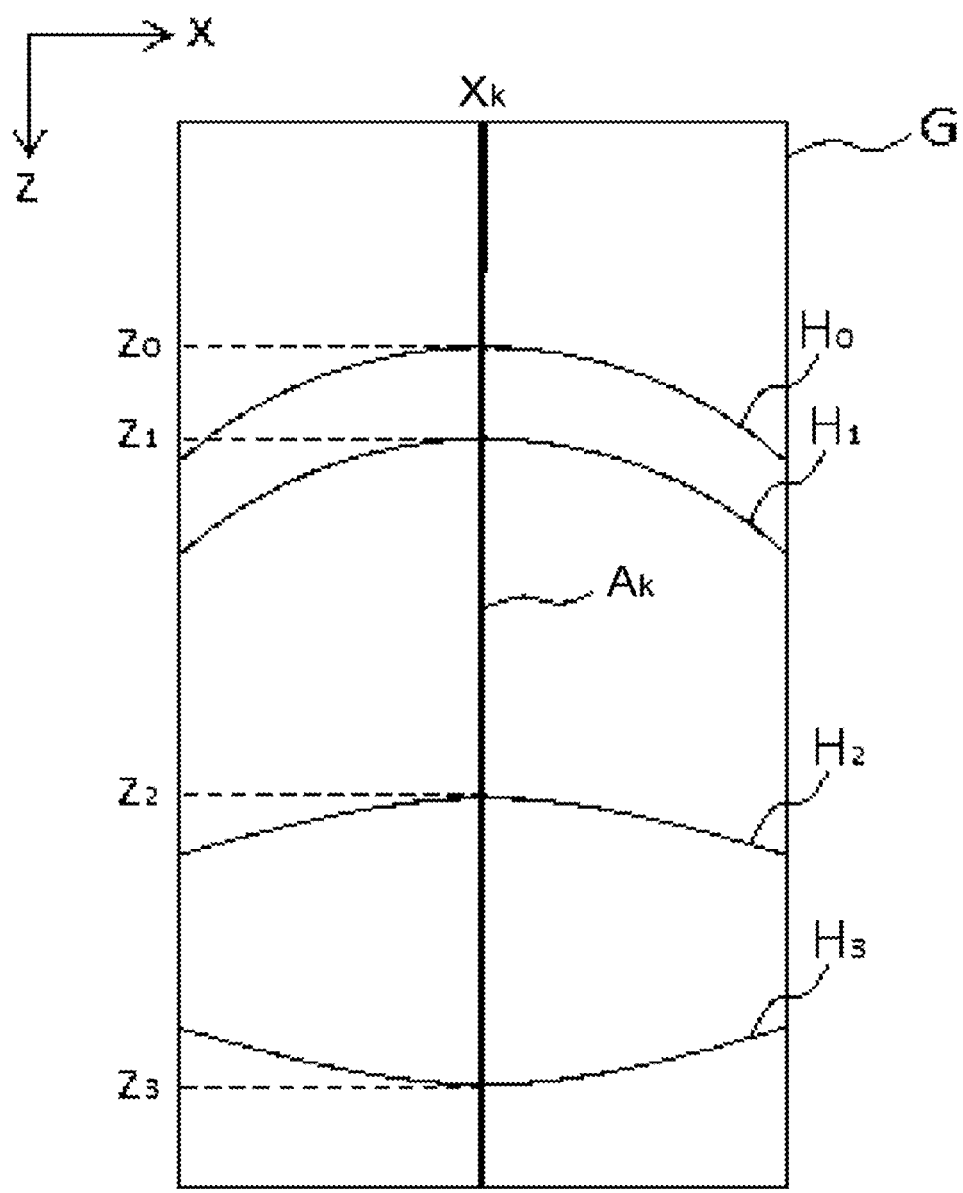
FIG. 4B is a schematic diagram for explaining an example of the operation of the accommodation function evaluation apparatus of the first embodiment.

Alternatively, the lens information generator 161 performs the process illustrated in FIG. 4B for each B-scan data (B-scan image) to acquire the position of the lens front surface image $H_2$ and the position of the lens rear surface image $H_3$ in the B cross section. Thus, the lens information generator 161 can generate the lens information including the positions acquired. Further, the lens information generator 161 analyzes the lens front surface image $H_2$ and the lens rear surface image $H_3$ to acquire information indicating the shape of the crystalline lens. Thereby, the lens information generator 161 can generate the lens information including the information acquired. Further, the lens information generator 161 may be capable of obtaining two-dimensional or three-dimensional position information and/or shape information of the front and rear surfaces of the crystalline lens based on the B-scan data related to a plurality of B cross sections. Thus, the lens information generator 161 can generate the lens information including the position information and/or shape information obtained.

(Evaluation Information Generator 162)

Based on the lens information generated by the lens information generator 161, the evaluation information generator 162 generates evaluation information related to the accommodation function of the subject's eye E. To perform this process, the evaluation information generator 162 includes a change information acquiring unit 1621 and an information generator 1622.

As described above, the lens information includes the position information and/or the shape information of the crystalline lens when the accommodative stimulus is being applied to the eye. The position information of the crystalline lens represents the position of the front surface and the position of the rear surface of the crystalline lens. The shape information of the crystalline lens represents the shape of the front surface and the shape of the rear surface of the crystalline lens. The thickness of the crystalline lens is changed by the application of the accommodative stimulus. This causes a change in the position and shape of the front surface as well as the position and shape of the rear surface.

When OCT is performed on the subject's eye E to which each of two or more accommodative stimuli are being applied, two or more pieces of lens information are generated correspondingly to the two or more accommodative stimuli. Based on the two or more pieces of lens information generated, the change information acquiring unit 1621 acquires change information indicating a change in the crystalline lens due to changes of the accommodative stimuli. An example of this process is described below.

It is assumed that first lens information corresponding to first accommodative stimulus, and second lens information corresponding to second accommodative stimulus are obtained. It is also assumed that each of the first and second lens information includes the position information of the front surface and the position information of the rear surface of the crystalline lens.

The change information acquiring unit 1621 calculates the difference between the position of the front surface and the position of the rear surface included in the first lens information. This process corresponds to, for example, the process of calculating the difference $z_3-z_2$ of two z-coordinate values $z_2$ and $z_3$ in FIGS. 4A and 4B. Thereby, the thickness of the crystalline lens in the corresponding A line is obtained. This process may be performed for the entire OCT data obtained (i.e., for all A-lines), or may be performed for only a representative position(s) (e.g., the corneal vertex, pupil center, or crystalline lens center). If the process is performed for two or more positions, the distribution of the thickness of the crystalline lens can be obtained.

By performing such process with respect to each of the first and second lens information, it is possible to obtain thickness information of the crystalline lens when the first accommodative stimulus is being applied to the eye (first thickness information), and thickness information of the crystalline lens when the second accommodative stimulus is being applied to the eye (second thickness information). The change information acquiring unit 1621 calculates a difference $\Delta T=|T_1-T_2|$ between thickness $T_1$ indicated by the first thickness information and thickness $T_2$ indicated by the second thickness information. Here, the absolute value is used for convenience to make the calculation result a non-negative value. Further, $\Delta T$ indicates the amount of change in the thickness of the crystalline lens due to a change in the accommodative stimuli. The amount of change $\Delta T$ in the thickness is an example of the change information.

Incidentally, when the thickness of the crystalline lens is obtained for two or more positions, the difference $\Delta T$ is calculated with respect to an A-line in first OCT data obtained when the first accommodative stimulus is being applied and an A-line in second OCT data obtained when the second accommodative stimulus is being applied, wherein the A-lines are associated with each other. The association of A-lines can be performed based on an anterior eye segment image captured by the imaging optical system 10, the first and second OCT data, or the like. Such a process enables to acquire the distribution of the change in the thickness of the crystalline lens caused by changes in the accommodative stimuli. The distribution of the change in the thickness is an example of the change information.

The change information acquired based on the position information of the crystalline lens is not limited to the change in the thickness, but may be any information acquired from the position information. Further, when the shape information of the crystalline lens is used, by performing a process similar to the process described above, it is possible to obtain the curvature, the change in the slope, or the like at a predetermined site (e.g., the vertex position of the front surface) of the crystalline lens. Alternatively, it is possible to obtain the distribution of the curvature, the change in the slope, or the like in a predetermined area (e.g., a partial region of the front surface), or the like.

Based on the change information acquired by the change information acquiring unit 1621, the information generator 1622 generates evaluation information. The change information includes a parameter such as change amount or change distribution as described above. The information generator 1622 generates the evaluation information with reference to, for example, association information that associates values of a parameter with degrees of the accommodation function. The association information is stored in the storage 120 in advance. The association information may be created by, for example, performing examination, which involves the application of accommodative stimulus and OCT, on a number of eyes (including healthy eyes and/or diseased eyes), and by statistically processing the clinical data thereby obtained. Incidentally, a plurality of pieces of association information may be prepared for predetermined attributes such as gender, age, disease name, characteristic values of an eyeball such that the plurality of pieces of association information can be selectively used according to the attribute of the subject, the subject's eye E, or the like.

A specific example of the association information is as follows: a first range of thickness change amount $\Delta T$ "$0 \leq \Delta T \leq \Delta T_1$" is associated with the degree of accommodation function "extremely low"; a second range of thickness change amount "$\Delta T_1 < \Delta T \leq \Delta T_2$" is associated with the degree of accommodation function "low"; and a third range of thickness change amount "$\Delta T_2 < \Delta T$" is associated with "normal" accommodation function. The information generator 1622 determines one of the first to third ranges to which the thickness change amount $\Delta T$ included in the change information acquired by the change information acquiring unit 1621 belongs. Further, the information generator 1622 specifies an evaluation result ("extremely low", "low" or "normal") associated with the range determined, and generates the evaluation information that includes the result of the evaluation.

If the storage 120 stores the reference data relating to the crystalline lens, the change information acquiring unit 1621 acquires the change information that indicates a change in the crystalline lens caused by the application of the accommodative stimulus based on OCT data obtained for the subject's eye E to which the accommodative stimulus is being applied and the reference data. This process may be the same as described above. Further, the information generator 1622 generates evaluation information based on the change information acquired by the change information acquiring unit 1621. This process may also be the same as described above.

(Optical Property Information Acquiring Unit 163)

The evaluation information may include information indicating the optical properties of the subject's eye E. In this case, the optical property information acquiring unit 163 can be provided. The optical property information acquiring unit 163 analyzes the optical properties of the subject's eye E obtained by the measurement optical system 30. The measurement optical system 30 measures the optical properties of the subject's eye E to which the accommodative stimulus is being applied. For example, the measurement optical system 30 measures the subject's eye E to which the first accommodative stimulus is being applied to obtain a first measurement value, and measures the subject's eye E to which the second accommodative stimulus is being applied to obtain a second measurement value. These measurements are carried out in parallel with or at different timing from OCT. Based on the first measurement value and the second measurement values obtained, the optical property information acquiring unit 163 acquires information indicating a change in the optical properties of the subject's eye E caused by the change in the accommodative stimuli. This information is referred to as optical property information.

The measurement optical system 30 of this embodiment functions as a refractometer for measuring the refractive power of the subject's eye. Based on the first measurement value and the second measurement values of the refractive power of the subject's eye, the optical property information acquiring unit 163 acquires the optical property information indicating a change in the accommodation amount of the subject's eye due to the change in the accommodative stimuli. This process is intended to calculate a difference between the first measurement value and the second measurement value. Incidentally, the actual accommodation amount per expected unit accommodation amount may be obtained by dividing the difference between the two measurement values by the amount of the change in the accommodative stimuli (i.e., expected accommodation amount). Further, the above examination may be performed a plurality of times to obtain a statistical value such as an average value, a variation, or the like.

While the eye refractive power is measured in this embodiment, other optical properties of the subject's eye may be measured. For example, the aberrations of the subject's eye can be measured. As one example of the configuration for performing the aberration measurement, Japanese Unexamined Patent Application Publication No. 2001-275972 disclosed by the present applicant teaches a wavefront sensor. The wavefront sensor irradiates a light beam from a point light source to the fundus of the subject's eye, detects the reflected light from the subject's eye with an area sensor through a Hartmann plate, and analyzes the distribution of a plurality of point images obtained by the detection, thereby obtaining the aberrations of various orders. With such a wavefront sensor, as well as the spherical degree and the astigmatic degree, higher order aberrations can be measured. Regarding the aberration of each order, the optical property information acquiring unit 163 acquires optical property information indicating a change in the aberration of the subject's eye due to the change in the accommodative stimuli based on the first measurement value and the second measurement value.

Further, if a light source with a high penetration depth in OCT is used, the return light of the measurement light includes information on a relatively wide range in the depth direction (z direction). The optical property information acquiring unit 163 can obtain the amount of aberrations generated in the range of the interior of the subject's eye E based on OCT data.

(User Interface 180)

A user interface 180 is a man-machine interface which provides information to the examiner and/or the subject, and which is used by the examiner and/or the subject to enter information and perform operation. The user interface 180 includes the display 181 and the operation unit 182.

(Display 181)

The display 181 includes, for example, a display device provided to the accommodation function evaluation apparatus 1. When a computer is connected to the accommodation function evaluation apparatus 1, the display 181 may include a display of the computer. The display 181 displays information under the control of the main controller 110.

(Operation Unit 182)

The operation unit 182 is used to operate the accommodation function evaluation apparatus 1 as well as entering information thereto. The operation unit 182 includes a hardware key such as a lever, a button, or the like provided to the accommodation function evaluation apparatus 1. When a computer is connected to the accommodation function evaluation apparatus 1, the operation unit 182 may include a manipulation device or an input device of the computer. The main controller 110 performs control in response to a signal input from the operation unit 182.

The display 181 and the operation unit 182 need not be configured as separate devices. It is possible to use a device that integrates the display function and the operation function, such as a touch panel. In this case, the graphical user interface (GUI) displayed on the display 181 is used as the operation unit 182.

[Operation]

Described below is the operation of the accommodation function evaluation apparatus 1.

(First Operation Example)

FIG. 5 illustrates a first operation example of the accommodation function evaluation apparatus 1. In this operation example, two accommodative stimuli are applied to the subject's eye E.

(S1: Perform Alignment)

First, the optical systems are aligned with respect to the subject's eye E. Specifically, first, the main controller 110 turns on the anterior eye illumination light source 11 and the alignment light source 21, and starts the operation of the image pickup device 16. Thereby, an anterior eye segment image of the subject's eye E, on which an alignment target image is projected, is obtained. The main controller 110 displays the anterior eye segment image on the display 181. As in the conventional manner, the user adjusts the position of the optical systems with reference to the position of the alignment target image rendered in the anterior eye segment image to perform alignment with the subject's eye E. Note that the main controller 110 can perform automatic alignment by analyzing the position of the alignment target image and adjusting the position of the optical systems.

(S2: Apply First Accommodative Stimulus)

After the completion of the alignment, the main controller 110 applies the first accommodative stimulus to the subject's eye E. Specifically, as well as turning on the target light source 51, the main controller 110 controls the target drive unit 50A to place the target light source 51 and the target plate 52 at a position corresponding to the first accommodative stimulus. Here, the position of the target light source 51 etc. corresponding to the first accommodative stimulus is set in advance. For example, the position may be set to a position corresponding to the far point of the subject's eye E.

(S3: Perform OCT and Optical Properties Measurement)

While the first accommodative stimulus is being applied to the subject's eye E, the main controller 110 performs control for OCT and optical properties measurement. Incidentally, these two operations may be performed at different timings, or at least the two may be performed in parallel.

OCT is described. First, the main controller 110 controls the reference drive unit 70A to move the reference mirror 74 and the lens 73 to positions where OCT data in a range that includes a target site of the crystalline lens is obtained. This process may be performed with reference to, for example, a live OCT image obtained from repetitive OCT. After the completion of the positioning of the reference mirror 74, the main controller 110 controls the light source unit 61 and the optical scanner 66 to perform OCT in an area of the subject's eye E including the target site. The detector 76 detects the interference light between the measurement light that has traveled through the subject's eye E and the reference light returning from the reference mirror 74. The image forming unit 150 forms OCT data (reflection intensity profile or image data) based on a signal output from the detector 76. The OCT data includes information indicating the form (position, shape, etc.) of the crystalline lens when the first accommodative stimulus is being applied to the eye. The main controller 110 stores the OCT data (first OCT data) thus obtained in the storage 120.

The optical properties measurement is described. First, the main controller 110 turns on the measurement light source 31. A measurement light beam output from the measurement light source 31 is reflected by the fundus of the subject's eye E, and detected by the image pickup device 16. The main controller 110 sends a signal output from the image pickup device 16 to the optical property information acquiring unit 163. This signal includes information indicating the size and shape of the cross section of the measurement light beam detected by the image pickup device 16. The optical property information acquiring unit 163 analyzes the signal, and thereby calculates the spherical degree, the astigmatism degree, the astigmatic axis, and the like of the subject's eye E. The main controller 110 stores the measurement value of the optical properties calculated in the storage 120. This measurement value indicates an optical property value of the subject's eye E to which the first accommodative stimulus is being applied, and is used as a first measurement value.

(S4: Apply Second Accommodative Stimulus)

After the completion of the OCT and the optical properties measurement, the main controller 110 applies the second accommodative stimulus to the subject's eye E. Specifically, the main controller 110 controls the target drive unit 50A to move the target light source 51 and the target plate 52, each placed in the position corresponding to the first accommodative stimulus, to a position corresponding to the second accommodative stimulus. The position of the target light source 51 etc. corresponding to the second accommodative stimulus is set in advance. For example, the position may be set to a position corresponding to the near point of the subject's eye E.

(S5: Perform OCT and Optical Properties Measurement)

While the second accommodative stimulus is being applied to the subject's eye E, the main controller 110 performs control for OCT and optical properties measurement. This process is performed as in step S3. Thereby, second OCT data for the subject's eye E to which the second accommodative stimulus is being applied, and a second measurement value of the optical properties of the subject's eye E are obtained. These pieces of information are stored in the storage 120.

(S6: Generate Evaluation Information)

The data processor 160 generates two pieces of lens information based on the first and second OCT data respectively obtained in steps S3 and S5. Based on these pieces of lens information, the data processor 160 acquires change information indicating the change of the crystalline lens due to the changes in the accommodative stimuli. Based on the change information thus obtained, the data processor 160 generates evaluation information.

In addition, based on the first and second measurement values respectively obtained in steps S3 and S5, the data processor 160 generates information (optical properties change information) indicating the changes in the optical properties due to the changes in the accommodative stimuli. This process includes, for example, the process of obtaining a difference between the first measurement value and the second measurement value. The optical properties change information thus obtained is included in the evaluation information.

The main controller 110 stores the generated evaluation information in the storage 120, and also displays it on the display 181. Thus, the process of this operation example ends.

(Second Operation Example)

Figure 6:
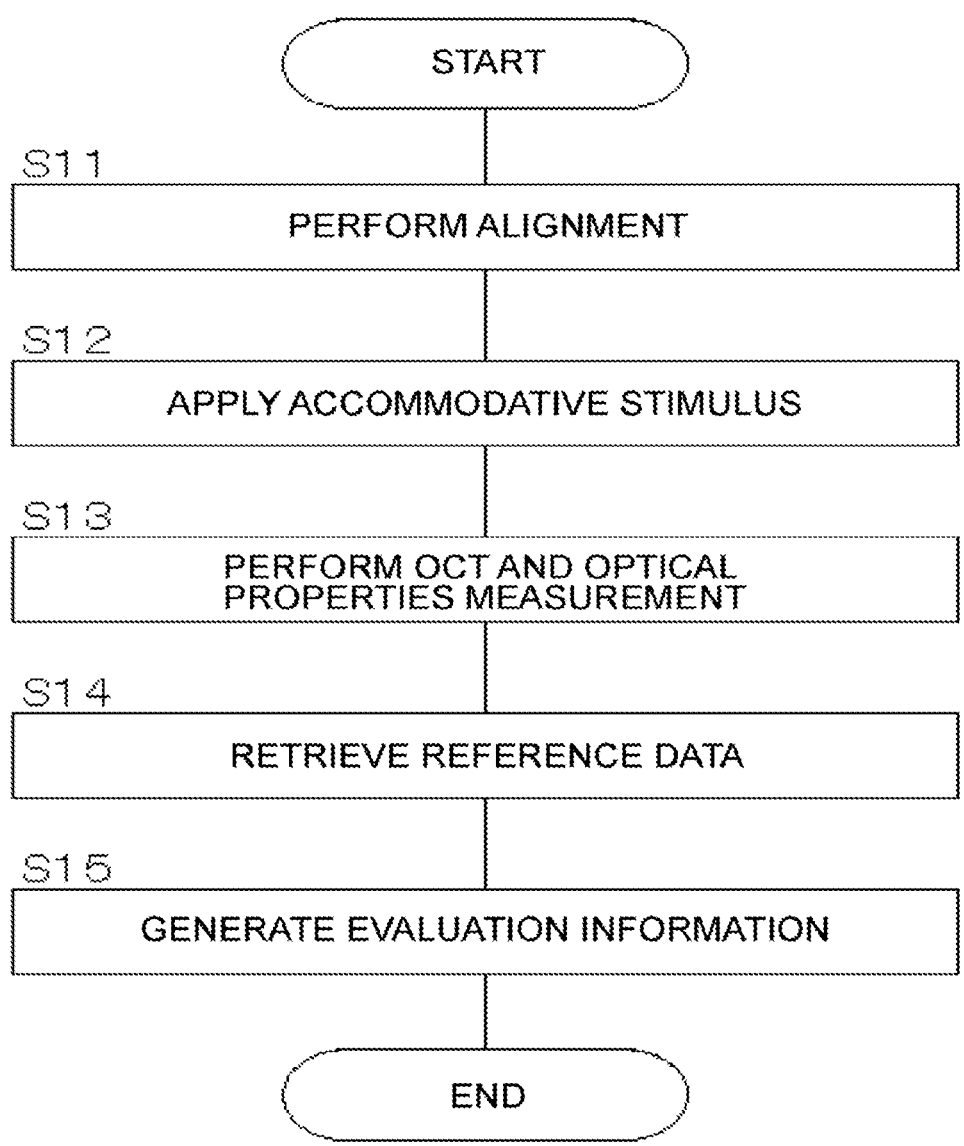
FIG. 6 is a flowchart illustrating an example of the operation of the accommodation function evaluation apparatus of the first embodiment.

FIG. 6 illustrates a second operation example of the accommodation function evaluation apparatus 1. In this operation example, a single accommodative stimulus is applied to the subject's eye E, and evaluation information is generated with reference to the reference data. Incidentally, it is assumed that the reference data includes information indicating the thickness of the crystalline lens when the accommodative stimulus corresponding to the far point is being applied to the eye. This information is information acquired in the past about the subject's eye E or standard information. The reference data may include a measurement value of the optical properties of the subject's eye E to which the accommodative stimulus is being applied.

(S11: Perform Alignment)

As in the first operation example, the optical systems are aligned with respect to the subject's eye E.

(S12: Apply Accommodative Stimulus)

After the completion of the alignment, the main controller 110 applies an accommodative stimulus corresponding to the near point of the subject's eye E to the subject's eye E. When the reference data includes information indicating the thickness of the crystalline lens corresponding to the near point, an accommodative stimulus corresponding to the far point of the subject's eye E may be applied to the subject's eye E.

(S13: Perform OCT and Optical Properties Measurement)

While the accommodative stimulus is being applied to the subject's eye E, the main controller 110 performs OCT and optical properties measurement. This process is performed as in the first operation example.

(S14: Retrieve Reference Data)

The main controller 110 retrieves the reference data stored in the storage 120 and sends it to the data processor 160.

(S15: Generate Evaluation Information)

Based on the OCT data obtained in step S13, the data processor 160 obtains the lens information (thickness information). Based on the thickness information obtained and the reference data (similarly, indicating the thickness of the crystalline lens) retrieved in step S14, the data processor 160 acquires change information indicating the change of the crystalline lens due to a change in the accommodative stimuli. Thus, the data processor 160 generates evaluation information based on the change information thus obtained.

In addition, the data processor 160 obtains the optical properties change information based on the measurement value of the optical properties obtained in step S13, and the measurement value contained in the reference data. The optical properties change information is included in the evaluation information.

The main controller 110 stores the generated evaluation information in the storage 120, and also displays it on the display 181. Thus, the process of this operation example ends.

[Actions and Effects]

A description is given of the actions and effects of the accommodation function evaluation apparatus according to the embodiment.

According to the embodiment, the accommodation function evaluation apparatus includes an accommodative stimulus applying unit, a measurement unit, and an analyzer. The accommodative stimulus applying unit has a function of applying an accommodative stimulus to a subject's eye. In this embodiment, the target projecting optical system 50 corresponds to the accommodative stimulus applying unit, and visual information (visual target) is used as the accommodative stimulus. The measurement unit performs OCT for a target site in the subject's eye including at least part of the crystalline lens. In this embodiment, the interference optical system 60 (and the image forming unit 150) corresponds to the measurement unit. The analyzer is configured to analyze data obtained by the OCT for the subject's eye, to which the accommodative stimulus is being applied, to generate evaluation information related to the accommodation function of the subject's eye. In this embodiment, the data processor 160 corresponds to the analyzer, and the evaluation information is generated by analyzing the reflection intensity profile, image data, or the like obtained by the OCT.

In this embodiment, the analyzer may include a lens information generator and an evaluation information generator. The lens information generator is configured to generate lens information indicating a position and/or shape of an area corresponding to part of the crystalline lens based on data obtained by the OCT of the subject's eye to which the accommodative stimulus is being applied. The area corresponding to part of the crystalline lens may include, for example, a front surface area corresponding to at least a portion of the front surface of the crystalline lens, and/or, a rear surface area corresponding to at least a portion of the rear surface of the crystalline lens. Further, the evaluation information generator may be configured to generate evaluation information based on the lens information generated by the lens information generator.

According to this embodiment, the state of a change in the form of the crystalline lens in response to the accommodative stimulus can be detected with high accuracy by using OCT. With this, it is possible to evaluate the accommodation function of the eye in detail.

In this embodiment, the accommodative stimulus applying unit may be configured to be capable of selectively applying two or more accommodative stimuli. In this case, the measurement unit may be configured to perform OCT with respect to the subject's eye, to which each of the two or more accommodative stimuli is being applied, to acquire two or more pieces of data. The lens information generator may be configured to generate two or more pieces of lens information based on the two or more pieces of data obtained by the measurement unit. The evaluation information generator may be configured to obtain change information indicating a change in the crystalline lens due to changes in the accommodative stimuli based on the two or more pieces of lens information generated, and generate evaluation information based on the change information thus obtained.

According to this embodiment, examination is performed while the accommodative stimulus is actually being changed. With this, the actual change in the form of the crystalline lens can be detected by using OCT. Accordingly, the accommodation function can be evaluated with a higher precision and accuracy.

In the embodiment, the accommodation function evaluation apparatus may be configured to perform evaluation of the accommodation function with the use of a predetermined reference data. The reference data is data indicating the reference position and/or the reference shape of a portion of the crystalline lens, and is stored in a storage in advance. The storage may be provided to the accommodation function evaluation apparatus, or it may be provided outside thereof. As an example of the latter, the storage may be a server (electronic medical record system, etc.) on a LAN in a medical institution. The evaluation information generator may be configured to acquire change information indicating a change in the crystalline lens caused by the application of the accommodative stimulus based on the reference data retrieved from the storage and the lens information generated by the lens information generator, and generate evaluation information based on the change information thus acquired.

According to this embodiment, the precision and accuracy may be reduced as compared to the case where examination is performed by actually changing the accommodative stimulus; however, accommodation function can be easily evaluated by the application of a single accommodative stimulus.

In the embodiment, the measurement unit may include a measurement optical system configured to measure the optical properties of the subject's eye to which the accommodative stimulus is being applied. Thereby, the optical properties of the subject's eye, to which the accommodative stimulus is being applied, can be obtained. Further, it is also possible to obtain a change in the optical properties of the subject's eye due to changes in the accommodative stimuli. With such a configuration, complex evaluation can be performed by taking into consideration both a change in the form of the lens and a change in the optical properties of the subject's eye.

<Second Embodiment>

A description is given of an embodiment that uses repetitive OCT measurement. The repetitive OCT measurement refers to a measurement technique in which OCT is repeatedly performed on substantially the same site of the subject's eye. With the repetitive OCT measurement, OCT data of substantially the same site of the subject's eye is repeatedly acquired. Incidentally, by repeating OCT at a predetermined repetition rate and repeatedly acquiring OCT image data, time series images of substantially the same site of the subject's eye are obtained. Besides, a moving image can be obtained by using a relatively fast repetition rate.

The accommodation function evaluation apparatus of this embodiment has a configuration similar to that of the first embodiment. The following description is given with reference to the drawings used in the first embodiment.

(First Operation Example)

Figure 7:
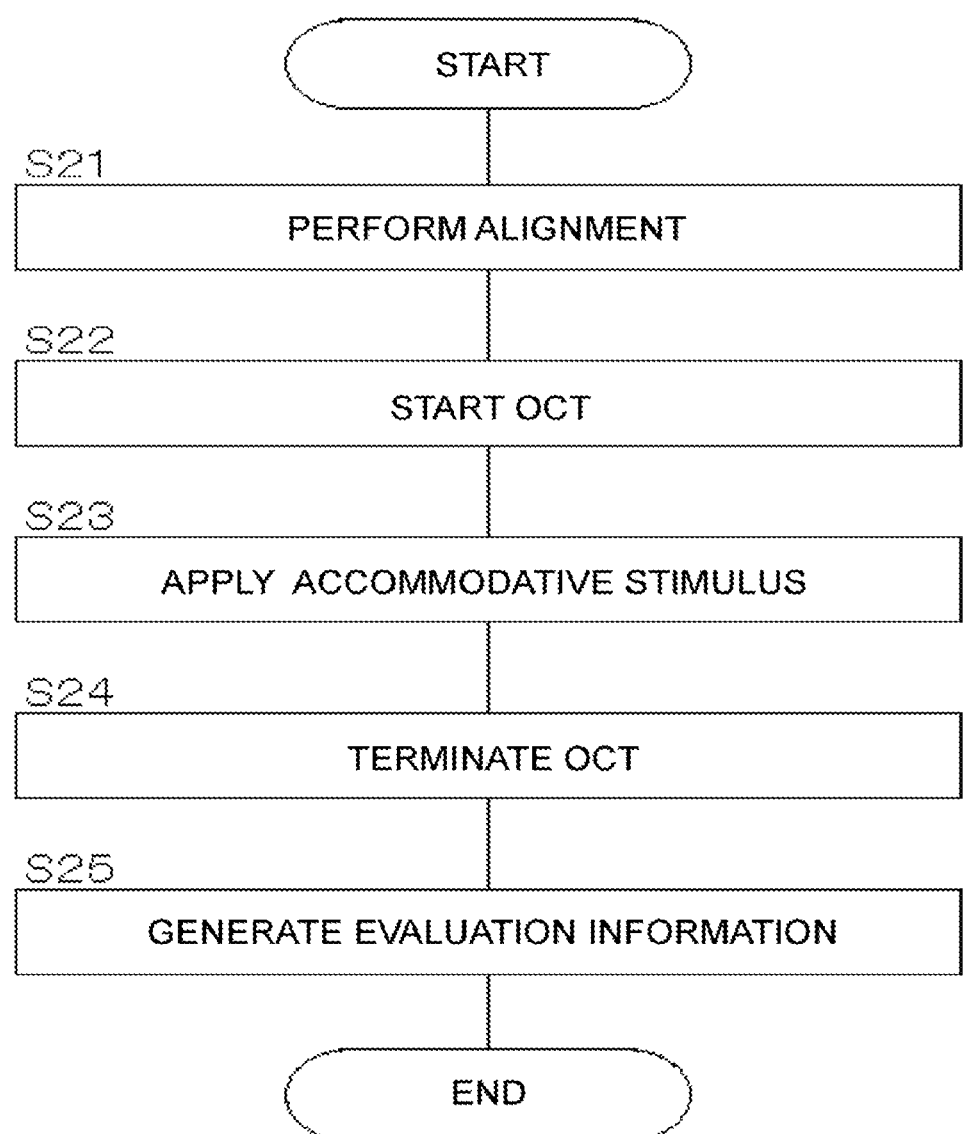
FIG. 7 is a flowchart illustrating an example of the operation of the accommodation function evaluation apparatus of the second embodiment.

In this operation example, OCT is performed on the subject's eye E to which a constant accommodative stimulus is being applied. The timing of applying the accommodative stimulus may be in any relationship with the timing of performing OCT. For example, the period in which the constant accommodative stimulus is being applied may be a part or the whole of the period in which OCT is being performed. The following description is given with reference to FIG. 7.

(S21: Perform Alignment)

As in the first embodiment, the optical systems are aligned with respect to the subject's eye E.

(S22: Start OCT)

After the completion of the alignment, the main controller 110 starts control for OCT.

(S23: Apply Accommodative Stimulus)

After the start of the OCT, the main controller 110 applies a predetermined accommodative stimulus to the subject's eye E. In this process, for example, the predetermined accommodative stimulus may be applied directly from a state where no accommodative stimulus is applied, or the state where no accommodative stimulus is applied may be gradually shifted to a state where the predetermined accommodative stimulus is applied.

(S24: Terminate OCT)

In response to a predetermined trigger, the main controller 110 terminates the OCT. Examples of such a trigger include, for example, an instruction issued by the user, a lapse of a predetermined time, occurrence of a predetermined event, and the like. The predetermined event is, for example, a change or a substantial steady state of a certain condition of the subject's eye E.

(S25: Generate Evaluation Information)

The data processor 160 generates evaluation information based on the OCT data acquired during steps S22 to S24.

In this operation example, the evaluation information indicates time series changes (i.e., time course, or chronological change) in the form of the crystalline lens caused by the application of the predetermined accommodative stimulus. In other words, the evaluation information indicates time series changes in the accommodative power. More specifically, the evaluation information indicates, for example; time series changes in the morphology (form) of the crystalline lens when the predetermined accommodative stimulus is applied; time series changes in the morphology of the crystalline lens in a period from before to after the predetermined accommodative stimulus is applied; time series changes in the morphology of the crystalline lens in a period from the predetermined accommodative stimulus is applied until the form of the crystalline lens is stabilized; or the fluctuation in the form of the crystalline lens after the form is stabilized.

An example of the process for obtaining such evaluation information is described. In this operation example, a plurality of pieces of OCT data arranged in time series is obtained. The data processor 160 performs the same process as in the first embodiment on each piece of the OCT data. For example, the data processor 160 obtains thickness information of the crystalline lens in each time phase based on the OCT data. Thereby, a data set indicating time series changes in the thickness of the crystalline lens is obtained. Further, based on the data set, the data processor 160 obtains a parameter such as the amount of the change in the thickness, the change rate of the thickness, the amount of fluctuations in the change of the thickness, the frequency of fluctuations in the change of the thickness, or the like. Then, for example, with reference to association information in which values of the parameter is associated with degrees of the accommodation function, the data processor 160 generates the evaluation information. The association information may be in a form similar to that described in the first embodiment.

The main controller 110 stores the generated evaluation information in the storage 120, and also displays it on the display 181. Thus, the process of this operation example ends.

(Second Operation Example)

In this operation example, OCT is performed while the accommodative stimulus is changed. As in the first operation example, the timing of applying the accommodative stimulus may be in any relationship with the timing of performing OCT. Besides, changes in the accommodative stimulus can be continuous changes or stepwise changes. The following description is given with reference to FIG. 8.

(S31: Perform Alignment)

As in the first embodiment, the optical systems are aligned with respect to the subject's eye E.

(S32: Start OCT)

After the completion of the alignment, the main controller 110 starts OCT.

(S33: Start Applying Accommodative Stimulus)

After the start of the OCT, the main controller 110 applies a predetermined initial accommodative stimulus to the subject's eye E. This process is performed, for example, in the same manner as the first operation example.

(S34: Change Accommodative Stimulus)

The main controller 110 changes the accommodative stimulus to be applied to the subject's eye E. For example, the accommodative stimulus may be automatically changed according to a preset process. Alternatively, the accommodative stimulus may be changed according to examiner's instructions.

As another example, the accommodative stimulus is changed according to the state of the accommodative power of the subject's eye E. This process is performed, for example, by analyzing OCT data acquired sequentially in real time. More specifically, the data processor 160 may acquire time series changes in the form (position, shape, etc.) of the crystalline lens based on time series changes of the peak positions in reflection intensity profiles acquired sequentially, or based on time series changes of the position or form of the image area of a target site (e.g., the front and rear surfaces of the crystalline lens) in a plurality of pieces of image data acquired sequentially. Based on the time series changes in the form of the crystalline lens (e.g., amount of change, change rate, degree of stability, etc.), the main controller 110 can change the accommodative stimulus according to a predetermined algorithm.

(S35: Terminate Application of Accommodative Stimulus, and Terminate OCT)

In response to a predetermined trigger, the main controller 110 terminates the application of the accommodative stimulus and terminates the OCT. For example, the trigger may be the same as in the first operation example. Besides, the timing of terminating the application of the accommodative stimulus may be the same as or different from the timing of terminating the OCT. In the latter case, an end trigger for the application of the accommodative stimulus and an end trigger for the OCT are individually issued.

(S36: Generate Evaluation Information)

Based on the OCT data acquired during steps S32 to S35, the data processor 160 generates evaluation information. This process may be performed in the same manner as in the first operation example.

The main controller 110 stores the generated evaluation information in the storage 120, and also displays it on the display 181. Thus, the process of this operation example ends.

[Actions and Effects]

A description is given of the actions and effects of the accommodation function evaluation apparatus according to the embodiment.

According to the embodiment, the accommodation function evaluation apparatus includes an accommodative stimulus applying unit, a measurement unit, and an analyzer. The accommodative stimulus applying unit has a function of applying an accommodative stimulus to a subject's eye. In this embodiment, the target projecting optical system 50 corresponds to the accommodative stimulus applying unit, and visual information (visual target) is used as the accommodative stimulus. The measurement unit performs OCT for a target site in the subject's eye including at least part of the crystalline lens. In this embodiment, the interference optical system 60 (and the image forming unit 150) corresponds to the measurement unit. The analyzer is configured to analyze data obtained by the OCT for the subject's eye to which the accommodative stimulus is being applied to generate evaluation information related to the accommodation function of the subject's eye. In this embodiment, the data processor 160 corresponds to the analyzer, and the evaluation information is generated by analyzing the reflection intensity profile or image data obtained by the OCT.

In this embodiment, the analyzer may include a lens information generator and an evaluation information generator. The lens information generator is configured to generate lens information indicating a position and/or shape of an area corresponding to part of the crystalline lens based on data obtained by OCT of the subject's eye to which the accommodative stimulus is being applied. The area corresponding to part of the crystalline lens include, for example, a front surface area corresponding to at least a portion of the front surface of the crystalline lens, and/or a rear surface area corresponding to at least a portion of the rear surface of the crystalline lens. The evaluation information generator is configured to generate evaluation information based on the lens information generated by the lens information generator.

According to this embodiment, a change in the form of the crystalline lens in response to the accommodative stimulus can be detected with high accuracy by using OCT. With this, it is possible to evaluate the accommodation function of the eye in detail.

In this embodiment, the measurement unit can perform OCT of the target site of the subject's eye repeatedly. In this case, the lens information generator can generate a plurality of pieces of lens information based on a plurality of pieces of data acquired by repetitive OCT. Further, the evaluation information generator may generate the evaluation information based on the plurality of pieces of lens information thus generated.

According to this embodiment, time series change in the morphology (form) of the crystalline lens can be obtained based on time series changes in the data acquired by repetitive OCT. Further, the evaluation information can be generated based on the time series changes in the morphology of the crystalline lens. Thereby, it is possible to provide a novel evaluation method on the basis of time series changes in the accommodation function of the subject's eye.

In the embodiment, the measurement unit may be configured to perform repetitive OCT for the subject's eye to which a constant accommodative stimulus is being applied.

According to this embodiment, it is possible to acquire time series changes in the accommodation function of the subject's eye, to which a constant accommodative stimulus is being applied. Further, it is possible to acquire time series changes in the accommodative power induced by the application of the constant accommodative stimulus. Thus, it is possible to provide a novel evaluation method based on such information.

In the embodiment, the accommodative stimulus applying unit may be configured to change the accommodative stimulus to be applied to the subject's eye at least in a part of the period in which repetitive OCT is performed.

According to this embodiment, it is possible to acquire time series changes in the accommodative power induced by a change in the accommodative stimuli applied. Thus, it is possible to provide a novel evaluation method based on such information.

In the embodiment, the measurement unit may include a measurement optical system configured to measure the optical properties of the subject's eye to which the accommodative stimulus is being applied. In this case, the measurement of the optical properties may be performed once or twice, or even more times. For example, by repeating the measurement of the optical properties at a predetermined repetition rate, time series changes in the optical properties can be obtained.

According to this embodiment, the optical properties of the subject's eye, to which the accommodative stimulus is being applied, can be obtained. Further, it is also possible to obtain changes in the optical properties of the subject's eye due to changes in the accommodative stimulus. Thus, complex evaluation can be implemented using both a change in the form of the crystalline lens and a change in the optical properties of the subject's eye.

[Modification]

The embodiments described above are mere examples for embodying or carrying out the present invention, and therefore susceptible to several modifications and variations (omission, substitution, addition, etc.), all coming within the scope of the invention.

While, in the above embodiments, the accommodative stimulus is applied to the subject's eye by using a visual target, the method of applying a stimulus to the eye and the content of the stimulus are not so limited. For example, electrical stimulation, ultrasonic stimulation, and light stimulation can be applied to the subject's eye. The electrical stimulation is applied by, for example, putting an electrode onto a stimulation site (ciliary muscles, etc.) or the vicinity thereof. The ultrasonic stimulation is applied by, for example, irradiating a stimulation site with ultrasonic waves using an ultrasonic vibrator. The light stimulation is applied by using a light source.

The site of the subject's eye, to which the stimulus is applied, is not limited to those related to the accommodation function (the crystalline lens, the Zinn's zonule, the ciliary body). In another example, the stimulus can be applied to the retina.

The invention claimed is:

1. An accommodation function evaluation apparatus comprising:
   an accommodative stimulus applying unit configured to apply an accommodative stimulus to an eye;

a measurement unit configured to perform optical coherence tomography for a target site in the eye including at least part of a crystalline lens: and an analyzer configured to analyze data obtained by the optical coherence tomography of the eye, to which the accommodative stimulus is being applied, to generate evaluation information related to accommodation function of the eye, the analyzer including a lens information generator configured to generate lens information indicating a position and/or shape of an area corresponding to part of the crystalline lens based on the data obtained by the optical coherence tomography of the eye, to which the accommodative stimulus is being applied, and an evaluation information generator configured to generate the evaluation information based on the lens information generated.

2. The accommodation function evaluation apparatus according to claim 1, wherein the accommodative stimulus applying unit is capable of selectively applying two or more accommodative stimuli, the measurement unit is configured to perform the optical coherence tomography of the eye, to which each of the two or more accommodative stimuli is being applied, to obtain two or more pieces of data, the lens information generator is configured to generate two or more pieces of lens information based on the two or more pieces of data obtained by the measurement unit, and the evaluation information generator is configured to obtain change information indicating a change in the crystalline lens due to a change in the accommodative stimuli based on the two or more pieces of lens information generated, and generate the evaluation information based on the change information obtained.

3. The accommodation function evaluation apparatus according to claim 1, wherein the evaluation information generator is configured to retrieve reference data indicating a reference position and/or reference shape of part of the crystalline lens from a storage, obtain change information indicating a change in the crystalline lens caused by application of the accommodative stimulus based on the reference data retrieved and the lens information generated by the lens information generator, and generate the evaluation information based on the change information obtained.

4. The accommodation function evaluation apparatus according to claim 1, wherein the measurement unit is configured to perform the optical coherence tomography for the target site repeatedly, the lens information generator is configured to generate a plurality of pieces of the lens information based on a plurality of pieces of data obtained by repetitive optical coherence tomography, and the evaluation information generator is configured to generate the evaluation information based on the plurality of pieces of the lens information generated.

5. The accommodation function evaluation apparatus according to claim 4, wherein the measurement unit is configured to perform the repetitive optical coherence tomography of the eye, to which a constant accommodative stimulus is being applied.

6. The accommodation function evaluation apparatus according to claim 4, wherein the accommodative stimulus applying unit is configured to change the accommodative stimulus to be applied to the eye at least in a part of a period in which the repetitive optical coherence tomography is performed.

7. The accommodation function evaluation apparatus according to claim 1, wherein the lens information generator is configured to generate the lens information related to a front surface area corresponding to at least part of a front surface of the crystalline lens, and/or a rear surface area corresponding to at least part of a rear surface of the crystalline lens.

8. The accommodation function evaluation apparatus according to claim 7, wherein the lens information generator is configured to generate the lens information related to positions of both the front surface area and the rear surface area, and the evaluation information generator is configured to obtain thickness information of the crystalline lens based on the position of the front surface area and the position of the rear surface area, and generate the evaluation information based on the thickness information obtained.

9. The accommodation function evaluation apparatus according to claim 1, wherein the measurement unit includes an interference optical system configured to split light from a light source into measurement light and reference light, and detect interference light between the measurement light that has traveled through the eye and the reference light, and an image forming unit configured to form an image of the target site based on a detection result of the interference light obtained by the interference optical system, and the analyzer is configured to analyze the image as the data to generate the evaluation information.

10. The accommodation function evaluation apparatus according to claim 1, wherein the measurement unit includes a measurement optical system configured to measure an optical property of the eye, to which the accommodative stimulus is being applied.

* * * * *